US00PP23452P2

(12) United States Plant Patent
Nishikawa

(10) Patent No.: US PP23,452 P2
(45) Date of Patent: Mar. 5, 2013

(54) ***DELOSPERMA* PLANT 'JEWEL OF DESERT ROSEQUARTZ'**

(50) Latin Name: *Delosperma cooperi*
Varietal Denomination: Jewel of Desert Rosequartz

(75) Inventor: Koichiro Nishikawa, Quito (EC)

(73) Assignee: Ron Van Dijk Consultancy B.V., Boskoop (NL)

( * ) Notice: Subject to any disclaimer, the term of this patent is extended or adjusted under 35 U.S.C. 154(b) by 0 days.

(21) Appl. No.: 13/199,787

(22) Filed: Sep. 9, 2011

(51) Int. Cl.
*A01H 5/00* (2006.01)

(52) U.S. Cl. ..... Plt./422

(58) Field of Classification Search ..... Plt./422
See application file for complete search history.

*Primary Examiner* — Howard Locker
(74) *Attorney, Agent, or Firm* — Penny J. Aguirre

(57) ABSTRACT

A new cultivar of *Delosperma* plant, 'Jewel of Desert Rosequartz', characterized by its compact and very horizontal plant habit, its relatively small leaves, its very floriferous and long blooming flowering habit, and its flowers that are light pink in color with white centers and yellow anthers.

2 Drawing Sheets

Botanical classification: *Delosperma cooperi.*
Variety denomination: 'Jewel of Desert Rosequartz'.

CROSS REFERENCE TO RELATED APPLICATIONS

This application is co-pending with U.S. Plant Patent Applications filed for plants derived from the same breeding program that are entitled *Delosperma* Plant Named 'Jewel of Desert Ruby' (U.S. Plant patent application Ser. No. 13/199,812), *Delosperma* Plant Named 'Jewel of Desert Moonstone' (U.S. Plant patent application Ser. No. 13/199,823), *Delosperma* Plant Named 'Jewel of Desert Topaz' (U.S. Plant patent application Ser. No. 13/199,826), *Delosperma* Plant Named 'Jewel of Desert Peridot' (U.S. Plant patent application Ser. No. 13/199,815), and *Delosperma* Plant Named 'Jewel of Desert Garnet' (U.S. Plant patent application Ser. No. 13/199,846).

BACKGROUND OF THE INVENTION

The present invention relates to a new and distinct cultivar of *Delosperma* plant, botanically known as *Delosperma cooperi* 'Jewel of Desert Rosequartz' and will be referred to hereinafter by its cultivar name, 'Jewel of Desert Rosequartz'. The new cultivar of *Delosperma* is a herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'Jewel of Desert Rosequartz' was selected in the Inventor's trial garden in November 2006 as a single unique plant from amongst the seedlings derived from self-crossing an unnamed plant from the Inventor's breeding program in may 2005. The Inventor's reference code for the parent plant is "A".

Asexual propagation of the new cultivar was first accomplished by softwood cuttings in summer of 2009 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Jewel of Desert Rosequartz' as a unique cultivar of *Delosperma.*

1. 'Jewel of Desert Rosequartz' exhibits a compact and very horizontal plant habit.
2. 'Jewel of Desert Rosequartz' exhibits relatively small leaves.
3. 'Jewel of Desert Rosequartz' exhibits a very floriferous and long blooming flowering habit.
4. 'Jewel of Desert Rosequartz' exhibits flowers that are light pink in color with white centers and yellow anthers.

The parent plant of 'Jewel of Desert Rosequartz', Ref. code "A", differs from 'Jewel of Desert Rosequartz' in having a more upright (less horizontal) plant habit, in blooming for a shorter time period, and in having flowers that are light yellow in color with white centers. 'Jewel of Desert Rosequartz' can be most closely compared to the cultivar 'Reiko' (not patented), which is similar to 'Jewel of Desert Rosequartz' in having a horizontal plant habit. 'Reiko' differs from 'Jewel of Desert Rosequartz' in having purple flowers and in blooming for a shorter period of time. 'Jewel of Desert Rosequartz' can also be compared to cultivars with co-pending patent applications from the same breeding program.

'Jewel of Desert Ruby' has red in color with deep pink and white centers and yellow anthers.

'Jewel of Desert Moonstone' has white flowers with yellow anthers.

'Jewel of Desert Topaz' has yellow-orange flowers with red petal tips, white-light purple centers, and yellow anthers.

'Jewel of Desert Peridot' has yellow flowers with white centers and yellow anthers.

'Jewel of Desert Garnet' has red-orange flowers with pink centers and yellow anthers.

BRIEF DESCRIPTION OF THE DRAWINGS

The accompanying colored photographs illustrate the overall appearance and distinct characteristics of the new *Delosperma*. The plant in the photograph is 3 months in age as grown in a 7-cm container in an unheated greenhouse in Noordwijkerhout, The Netherlands.

The photograph in FIG. 1 provides a side view of 'Jewel of Desert Rosequartz' in bloom.

Figure 1:
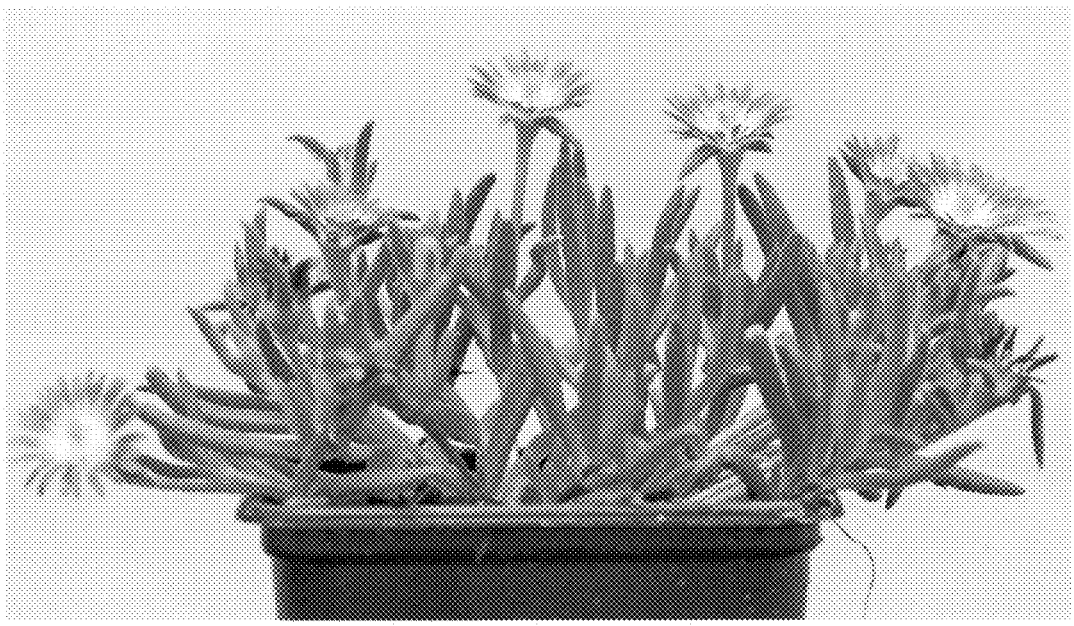
Figure 2:
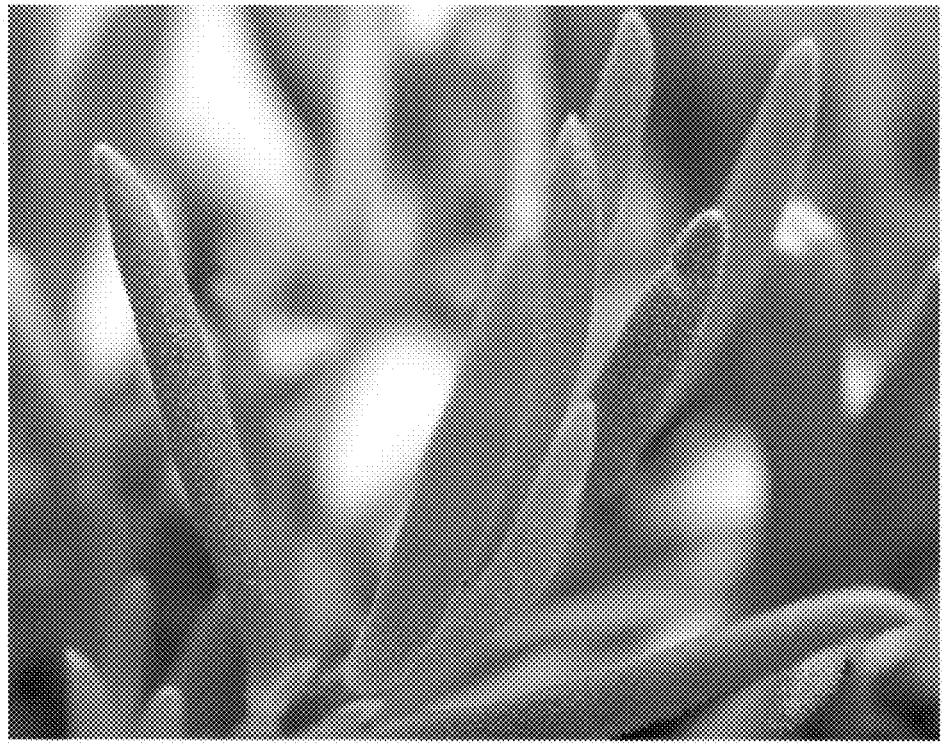

The photograph in FIG. 2 provides a close-up view of the foliage of 'Jewel of Desert Rosequartz'.

Figure 3:
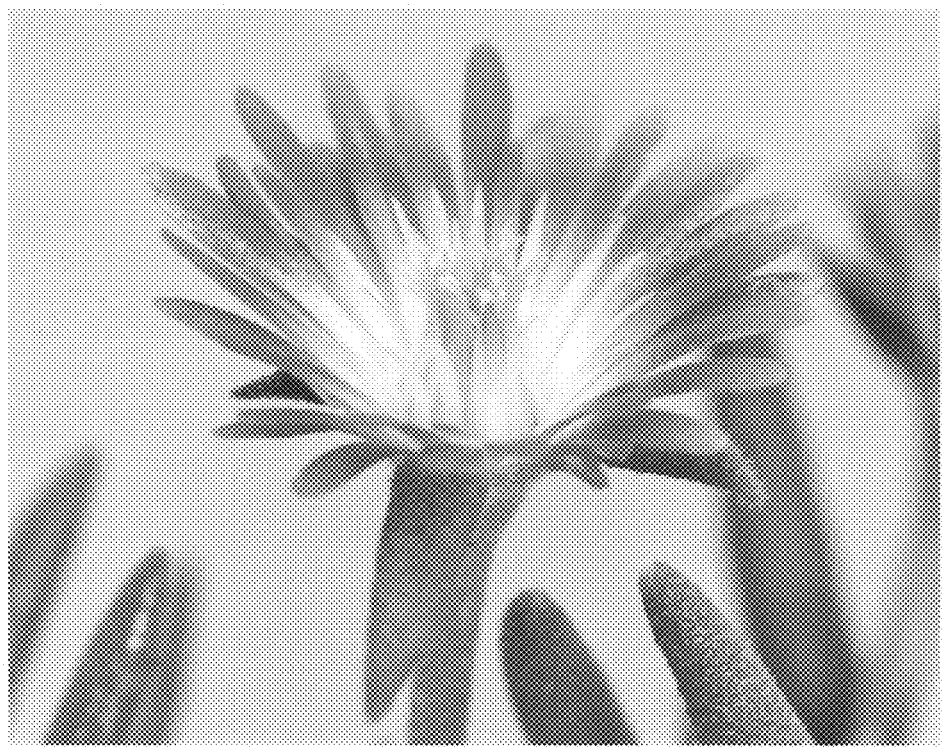

The photograph in FIG. 3 provides a close-up view of a flower of 'Jewel of Desert Rosequartz'.

The colors in the photographs may differ slightly from the color values cited in the detailed botanical description, which accurately describe the colors of the new *Delosperma*.

DETAILED BOTANICAL DESCRIPTION

The following is a detailed description of six week-old plants of the new cultivar as grown in 7-cm containers in a unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid April to mid September in Noordwijkerhout, The Netherlands.

*Plant type.*—Herbaceous perennial.

*Plant habit.*—Compact, well-spreading, horizontal.

*Height and spread.*—About 6.2 cm in height and about 12.8 cm in diameter with mature plants reaching up to 10 cm in height and 30 cm in spread.

*Cold hardiness.*—Observed to be hardy to U.S.D.A. Zone 7.

*Diseases.*—No more susceptible or resistant to diseases than other *Delosperma cooperi* varieties, diseases are typically not a problem for *Delosperma cooperi*, except when grown with too much moisture.

*Root description.*—Fibrous roots.

*Propagation.*—Softwood cuttings.

*Growth habit.*—Moderately vigorous.

Stem description:

*Shape.*—Round.

*Stem color.*—145C, older stems a blend of 150D, slightly tinged with 174B.

*Stem size.*—Lateral branches; an average of 3.0 cm in length and 2 mm in diameter.

*Internode length.*—An average of 14 mm.

*Stem substance.*—Succulent.

*Stem surface.*—Moderately glossy, sparsely to moderately pubescent with very short glandular hairs; an average of 0.5 mm in length and about 155C in color.

*Branching habit.*—Basal branching with an average of 12 lateral branches per stem.

Foliage description:

*Leaf shape.*—Ligulate, triangular in diameter.

*Leaf substance.*—Succulent.

*Leaf division.*—Simple.

*Leaf base.*—Cuneate.

*Leaf apex.*—Acute.

*Leaf venation.*—No veins visible.

*Leaf margins.*—Entire.

*Leaf arrangement.*—Opposite.

*Leaf surface* (*Upper and lower surface*).—Slightly glossy, slightly pubescent with very short glandular hairs; an average of 0.2 mm in length, 155C in color.

*Leaf color.*—Young upper and lower surface; 144A, base 144C, mature upper and lower surface; 143B, base 144A.

*Leaf size.*—About 3.3 cm in length and 4 mm in width.

*Leaf quantity.*—Average of 6 (3 pairs) per lateral branch.

*Leaf attachment.*—Sessile.

Inflorescence description:

*Inflorescence type.*—Flowers solitary.

*Flower number.*—An average of 4 per lateral stem, 48 per plant in a 7-cm container.

*Flower fragrance.*—Faint, sweet and pleasant.

*Flower aspect.*—Outward to upright.

*Flower longevity.*—A few days.

*Flower type.*—Single.

*Flower size.*—Average of 2.3 cm in diameter and 0.9 cm in depth.

*Flower buds.*—Broadly ovate to oblong in shape, an average of 10 mm in length and 6 mm in diameter, color; 144C, tip 143B.

*Calyx.*—Rotate in shape, average of 5 mm in depth and 1.8 cm in diameter.

*Sepals.*—5, rotate, narrow ovate in shape, margin entire, an average of 8 mm in length and 2.5 mm in width, broadly acute apex, broadly cuneate base, surface is smooth and dull, color young upper and lower surface; 144C, tip 143B, color mature upper and lower surface; 137C.

*Petals.*—An average of 30 per flower, rotate and slightly curved, narrowly oblanceolate in shape, surface is smooth and moderately to highly glossy on both surfaces, margin entire, apex obtuse, base cuneate, an average of 1.0 cm in length and 1.5 mm in width, color; opening flowers upper surface; 52B, base 56A blending into 155A at very base, opening flowers lower surface; 64D, fully opened flower upper surface; a blend of 64A and 71A, base a blend of 37C and 37D, fully opened flower lower surface; 64C, base 65A, fading upper surface; 64D, base 37D, fading lower surface 64D, base 65C.

*Petaloids.*—An average of 30 per flower, rotate and near vertical surrounding stamens, lanceolate in shape, moderately to highly glossy on both surfaces, margin entire, apex obtuse, base truncate, an average of 4 mm in length and 1 mm in width, color mature upper and lower surface; 11D blending into 155A at very base, color immature upper and lower surface; 11B blending into 155A at very base, non fading.

*Peduncle.*—Average of 2.7 cm in length and 15 mm in diameter, straight on top of lateral branch at 0°, color; 150D, tinged with 152A, surface moderately glossy, sparsely to moderately pubescent with very short glandular hairs.

Reproductive organs:

*Pistils.*—About 5, an average of 2 mm in length, triangular shaped stigma, style and stigma (not distinguishable) are an average of 2 mm in length and 144A in color, ovary is 144A in color.

*Stamens*.—Average 60, anthers are dorsifixed and oblong in shape, an average of 0.5 mm in diameter and 3 mm in length, filaments are 155D in color, anther is 13A to 13B in color, pollen is moderate in quantity and 14A to 14B in color.

*Fruit*.—Fruit and seed production was not observed under the conditions tested.

It is claimed:

1. A new and distinct variety of *Delosperma* plant named 'Jewel of Desert Rosequartz' as described and illustrated herein.

* * * * *